United States Patent [19]

Beaver

[11] Patent Number: 4,715,105
[45] Date of Patent: Dec. 29, 1987

[54] METHOD OF PREPARATION OF PACKED FIBER GLASS REACTION VESSEL

[75] Inventor: Richard P. Beaver, Library, Pa.

[73] Assignee: PPG Industries, Inc., Pittsburgh, Pa.

[21] Appl. No.: 852,866

[22] Filed: Apr. 16, 1986

Related U.S. Application Data

[63] Continuation of Ser. No. 750,445, Jul. 1, 1985, Pat. No. 4,657,742.

[51] Int. Cl.$^4$ ............................................. B32P 17/00
[52] U.S. Cl. .................................. 29/419 G; 29/433; 29/283.5; 29/520
[58] Field of Search ................ 29/433, 520, 452, 517, 29/283.5, 419 R, 419 G; 422/46, 48, 240; 55/158, 386; 502/527; 210/321.1, 321.3, 508, 509, 198.2

[56] References Cited

U.S. PATENT DOCUMENTS

| | | | |
|---|---|---|---|
| 1,455,953 | 5/1923 | Wright | 29/520 UX |
| 1,463,015 | 7/1923 | Guay | 29/517 X |
| 3,157,143 | 11/1964 | Van Embden | 29/517 UX |
| 3,510,934 | 5/1970 | Koelichin | 29/520 X |

Primary Examiner—Charlie T. Moon
Attorney, Agent, or Firm—John E. Curley

[57] ABSTRACT

A packed tube of generally parallel aligned fibers is described, wherein the fibers are packed therein at densities of 60 to 100 percent of the theoretical packing density based on the fiber diameters used based on the selected fiber pitch pattern and preferably at 70 to 100 percent of the theoretical. Glass fibers which can be porous and/or hollow are preferred.

3 Claims, 10 Drawing Figures

METHOD OF PREPARATION OF PACKED FIBER GLASS REACTION VESSEL

This is a continuation of application Ser. No. 750,445 filed July 1, 1985, now U.S. Pat. No. 4,657,742.

The present invention relates to novel reaction vessels and to methods of preparing them. More particularly, the invention relates to novel packed columns containing fibers oriented and packed in a manner rendering them suitable for use as biosupports, catalyst supports, chromatography applications and other similar uses. Still more particularly, the present invention relates to novel packed columns of glass fibers which may be porous and/or hollow for use as biosupports in chromatography columns, catalytic reactors and other like applications.

BACKGROUND OF THE INVENTION

Many current chemical and biochemical processes involve fluid contact at a solid or supported liquid surface. Some nonexclusive examples of these processes include high pressure liquid chromatography (HPLC), membrane processes, filtration application and catalysis. A wide variety of materials have been used as the solid phase or support, including diatomaceous earth, alumina, glass beads, and cellulosic, synthetic or glass fibers.

Spherical particles such as glass beads, and particulate materials such as diatomaceous earths, alumina and the like have found particular utility in reactors as supports for biological species such as in enzyme, protein and cell immobilization. Particulates of these materials and glass beads have also been used in catalytic reactors and liquid phase chromatography. Problems occurring utilizing particulates is the difficult and tedious process involved in packing columns with these materials. The particles tend to bridge during filling and often require high pressure applied to them when packed in columns. A chromatography column utilizing glass beads, for example, is described in U.S. Pat. No. 4,165,219. Packing of fibers in loose configuration in random form have found some utility in providing filter tubes such as those described in U.S. Pat. No. 4,210,540.

While solid supports have been employed in a multitude of chemical applications, the utilization of fibers, and in particular, glass fibers having substantial amounts of porosity imparted to them and/or being hollow in addition to being porous are particularly attractive. The attractiveness of porous and porous and hollow glass fibers results from the fact that they are generally inert to contamination by organics and are generally inert to biochemical contamination. Further, glass fibers can be cleaned readily with reagents without damage and can be, therefore, subjected to continuous reuse after cleaning.

One difficulty encountered in utilizing any fibers, and especially glass fibers, is the inability to pack sufficient quantities of fibers in a confined area in a convenient manner. Loading such fibers in a column or tube for use in a reaction vessel such as a chromatography column or as a part of a chemical reaction vessel, for example, a multi tube fixed bed catalytic reactor, or for other similar uses has heretofore not been of practical value. In particular, in loading a tube or column with glass fibers, care must be taken to insure that the fibers do not substantially abraid each other or abraid the sides of the columns to be packed. Abrasion can cause extensive damage to the glass fiber support material. Further, care must be taken to avoid any fusing or cracking of fibers that are placed in the tubes.

SUMMARY OF THE INVENTION

By virtue of the instant invention, applicant has produced novel reaction vessels packed with fibers in such a manner that the fibers generally run parallel with respect to each other. The fibers can be concentrated in dense bundles to fill columns for use as reaction vessels. Further using the methods of the instant invention, glass fibers can be used as packing in the form of solid glass fibers, porous glass fibers, or hollow and porous glass fibers.

It is an object of the invention to provide packed tubes containing fibers, which are packed with a very high, controlled packing density higher than heretofore practical.

It is a further object of the invention to provide packed tubes which contain fibers generally oriented in parallel with respect to each other and the tube, at loadings of at least sixty (60) percent of the theoretical maximum packing density based on fibers used and tube diameters, preferably 70 to 100 percent of the theoretical maximum packing density.

It is still another object of the invention to provide packed tubes of parallel aligned glass fibers using porous, solid, hollow or porous and hollow glass fibers.

Another object of the invention is to provide packed tubes of parallel glass fibers which are porous, solid, hollow or porous and hollow at packing densities of at least sixty (60) percent of the theoretical maximum packing density based on the fiber and tube diameter employed, preferably 70 to 100 percent of the theoretical maximum packing density.

Still another object of the invention is to provide packed tubes of parallel glass fibers which can be adjusted in surface area for any particular application by adjusting the porosity of the fibers while the fibers are contained in the tube in which they are packed.

A still further object of the invention is to provide a convenient method of packing glass fibers in tubes without damage while maximizing the density of the fibers packed in a given tube.

A still further object of the invention is to provide methods of packing parallel glass fibers in a tube to provide packed tubes that can be adjusted to any given length desired.

A still further object of the invention is to provide a packed tube of fibers that can produce a high density packed column having good flow characteristics with respect to fluids fed therethrough.

A further object of the invention involves providing a method of tube packing that permits tubes to be packed at consistent fiber packing densities.

Another object of the invention involves providing packed tubes of parallel glass fibers having pores therein for use in immobilizing cells, proteins and enzymes thereon.

These and other objects of the invention will become apparent from the ensuing description.

The packed tubes of the instant invention contain fibers throughout their length generally in parallel with the long axis of the tube and with each other. The fibers packed in the tubes may be solid, solid with pores provided in them, hollow in configuration with a central lumen and in some instances, hollow with pores provided in the fibers surrounding the lumen. The pores provided in the hollow fibers may be sufficient in depth to communicate with the lumen or of a depth that does not. In the preferred embodiment of the invention, the fibers employed are comprised of glass and in the ensuing description, the invention will be described for convenience in terms of glass fibers, it being understood that fibers other than glass can be used.

The packed tubes are typically packed densely enough to inhibit substantial movement of the fibers therein. Packing density can be varied but typically, based on the diameter of the fibers used and the internal diameter of the tube, are in the range of 60 to 100 percent, preferably 70 to 100 percent, of the theoretical maximum packing density, based on the chosen fiber pitch, which is usually a triangular pitch pattern.

The packed tubes of the invention having fibers oriented generally parallel to each other and to the tube housing them provides ease of flow of fluids through the tubes since tortuosity is minimized. Even in instances where a fiber bundle has a twist imparted to it, fluid flow is urged in the direction of the tube and little or no tortuosity will be encountered.

The methods of the instant invention providing for tube packing are such that fiber damage when glass fibers are employed is minimized while high packing densities are realized with little or no difficulty. The methods involve in one embodiment preparing a densely packed bundle of fibers using a casing capable of axial compression under heat to permit packing fibers in the casing, shrinking or collapsing the casing to hold one end of the fiber bundle in dense packages and providing means at one end of the fiber bundle to draw it and its associated fiber bundle into a tube of given diameter.

In the preferred embodiment of the invention, a fiber bundle of a given number of fibers is placed in a tube of a fixed internal diameter which is larger than the desired final tube diameter. That tube is then drawn through a die in which the tube is reduced in internal diameter to the desired diameter with the fibers thereby being concentrated in density as the final diameter tube is formed. The final packed tube is then cut to the lengths desired and the cut ends machined to permit their use in a variety of apparatus. While one pass through a die will usually suffice, it is within the contemplation of the invention that several passes through the reducing die may be required.

BRIEF DESCRIPTION OF THE DRAWINGS

For a more complete understanding of the invention, reference is made to the accompanying drawings in which.

DETAILED DESCRIPTION OF THE INVENTION

Preparation of the Fibers

Figure 1:
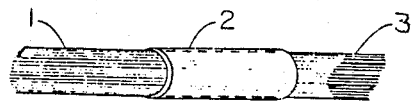
FIG. 1 is a diagrammatic illustration of the first step in the preparation of packed tubes in accordance with the first embodiment of the methods of the instant invention.

The glass fibers used in preparing the preferred packed reaction vessels of the instant invention may be solid or they may be solid fibers that have been rendered porous or they may be hollow fibers or fibers which are hollow and also have been treated to render them porous. The glass compositions utilized in forming the fibers will vary depending upon the particular type of fiber that is desired and the use to which the packed tube is to be put. In general, any glass composition which is suitable for use in the manufacture of glass fibers can be employed. Thus, E-glass fibers, 621-glass fibers, or any other glass fibers containing from 5 to 28 percent $B_2O_3$ by weight of the glass composition can be utilized. Glasses of these types are described in U.S. Pat. Nos. 2,106,744; 2,334,961; 2,571,074; 3,650,721, all herein incorporated by reference. Glasses having a low $B_2O_3$ content such as described in U.S. Pat. No. 4,166,747 as well as glasses that contain neither fluorine nor boron such as those described in U.S. Pat. No. 3,847,626 all incorporated herein by reference, and glasses such as described in applicant's assignee's copending application Ser. No. 562,945, filed Dec. 19, 1983, now abandoned, may also be employed.

In general, these fibers can be produced by any of the conventional methods utilized in the prior art to form glass fibers. The fibers can be formed from glass compositions which have been formed from batch ingredients typically utilized in the fiber glass manufacturing direct melt processes. They may also be formed from preformed glass marbles containing the desired glass composition and melted in a marble melt container called a bushing.

In the direct melt process, the glass ingredients are mixed together and melted in a direct melt furnace. The resulting molten glass is passed to a forehearth and is then fiberized from containers called bushings, which are mounted on the underside of the forehearth. The bushings have a multiplicity of holes in the bottom that form the individual fibers from molten glass flowing through the holes. Typically, the holes have a tip depending downwardly to regulate by its diameter and the speed at which the fibers are drawn the ultimate diameter of the formed fibers. The fibers are then typically gathered together into a single strand after passing over an applicator surface. The bushings are typically electrically heated to maintain the glass molten. Various processing aids such as lubricants, coupling agents and the like are applied to the fibers as they are drawn from the bushing over the applicator surface. The aforementioned methods of preparing glass fibers are well known in the art. U.S. Pat. No. 3,082,614 describes one direct melt system. A marble melt bushing is shown on pages 90–91 of Lowenstein, "The Manufacturing Technology of Continuous Glass Fibers", 1973, Elsevier Publishing Co.

In those instances where porous fibers are to be utilized, porosity is provided to the glass fibers by employing any of many well known techniques. Thus, in treating the borosilicate glasses, for example, glass is typically heat treated for a given period of time to provide for phase separation of the glass components in the fiber. After phase separation, the fibers are treated with mineral acid to leach out the borosilicate rich phase or leachables to provide pores of specific diameters. One such system is described in assignee's U.S. Pat. No. 3,630,700 in connection with leaching glass particles. That same system can be used to leach glass fibers. In the case of E-glass, using that system the heat treatment step is not recommended prior to leaching and is therefore not used. Other similar leaching processes are described in U.S. Pat. Nos. 3,650,721 and 4,042,359. In utilizing the principles described in these patents, glass fibers which are solid or hollow can be treated to provide porosity thereto. In the case of hollow fibers where it is desired, the leaching may be conducted for a sufficient time to provide pores that communicate with the lumen of the hollow fibers. Hollow fibers can be prepared conveniently utilizing the method described in the U.S. Pat. No. 3,268,313. Assignee's U.S. Pat. No. 3,510,393 claims a hollow glass fiber that can be used in preparing the reaction vessels of the instant invention as it is or after it has been further treated to render the hollow fibers porous. In some instances, it is possible to render fibers porous using water alone without the utilization of an acid leach and typically in these instances, the leached glass normally contains less than 5 percent $B_2O_3$ and may contain small quantities of alkali metal oxide, i.e., less than 1 percent.

Further, in the case of glasses containing large quantities of $B_2O_3$, i.e., above 28 percent by weight, water may be used to impart porosity since it readily leaches the extractables from these types of glasses. Thus, a glass having $B_2O_3$ in the range of 28 to 54 percent can be leached with water with or without heat treating the glass.

It has also been a practice in the art in rendering glass fibers porous by an acid leach to enlarge the pores if the pores are of insufficient diameter for the use to which the fibers are to be employed after the acid leach by treating the glass with an alkali leach. Thus, subsequent treatment of the porous glass fiber with alkali solutions such as alkali metal hydroxides can render the pores larger by dissolving from the glass structure of the glass fiber quantities of materials that were not readily leachable using acid such as some of the $SiO_2$ and $Al_2O_3$ constituents normally present after the acid leach.

The fibers utilized in packing the columns can be in fiber form, they may also be in strand form or roving form. It will be understood by skilled artisans that a fiber means an individual filament, strand means a group of filaments gathered into a single unitary bundle and roving means a plurality of strands which have been combined into a single bundle.

Column Packing

In preparing the novel reaction vessels of the instant invention, one method employed to provide for a dense packing of fibers in the column will be described with reference to FIGS. 1–6.

Figure 2:
FIG. 2 is a diagrammatic illustration of the second fabrication step of the first method embodiment.
Figure 3:
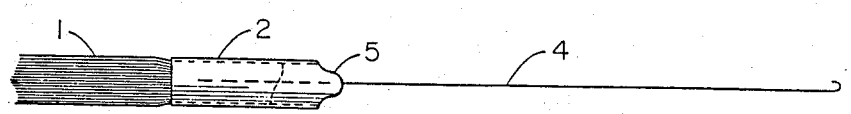
FIG. 3 is a diagrammatic illustration of the third fabrication step of the first method embodiment.
Figure 4:
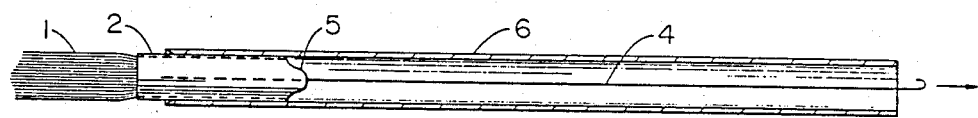
FIG. 4 is a diagrammatic illustration of the fourth fabrication step of the first method embodiment.
Figure 5:
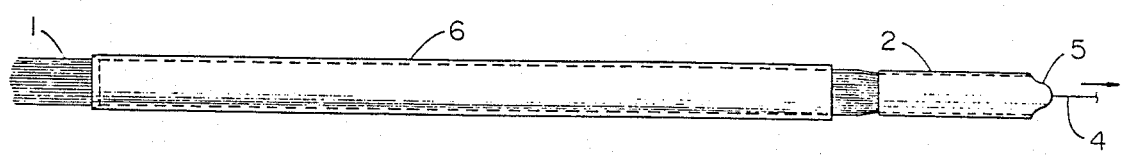
FIG. 5 is a diagrammatic illustration of the fifth step of the first method embodiment.
Figure 6:
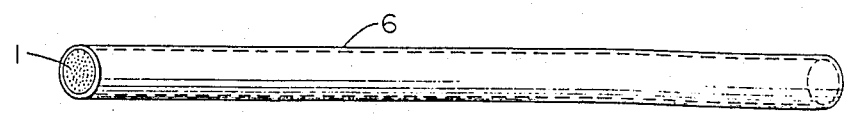
FIG. 6 is a diagrammatic illustration of a packed tube of the instant invention fabricated by the first method embodiment.

Turning to the drawings and FIGS. 1–6 in particular, a plurality of glass fibers 1, sufficient to pack a column of a given internal diameter, are aligned lengthwise and generally parallel to each other and enveloped in a heat shrink tubing 2, made out of a heat shrinkable polyolefin, polyethylene for example. The diameter of the tubing of the polyolefin is selected to be larger in size than the diameter of the tube to be packed but will, when heat shrunk, conform to the internal diameter of the column to be packed. The ends of the fibers passing through the polyolefin tubing material are dipped in a polyester resin that is preferably room temperature curable and the resin is permitted to wick along the fiber length for as distance of about 2 inches. After the resin 3 has wicked along the fiber length the desired distance, the shrink tubing is moved towards the end of the fiber bundle to a point slightly beyond the end of the bundle end as shown in FIG. 2. This results in the the end of the shrink tubing also being filled with resin. A rigid wire or rod 4, is inserted into the resin and penetrates the fiber bundle. The heat shrink tubing 2, then has heat applied to it causing it to shrink before the resin 3 hardens which collapses the fiber bundle 1, and the resin 3, around the area of the shrink tubing. In conducting this heat shrinking operation, the end of the tubing 3, will shrink considerably more than the part of the tubing surrounding the fiber bundle 1, causing the tubing at the extremities of the fiber bundle to angle inwardly and to form a conical shape at the end. When the resin 3, has hardened, the collapsed tubing is cut away from the resin leaving a cone shaped resin plug 5 with a wire 4 embedded in the resin. The wire 4 is then passed into the tube 6 that is to be packed. The wire 4 is pulled through the tube 6 and the resin plug 5 and the remaining fibers, which are loosely bundled beyond plug 5 are drawn into the tube 6. The wire 4 is pulled through the tube until the plug 5 protrudes beyond the end of the column. The resin plug 5 is then cut from the fiber bundle and the tube contains a bundle of densely packed fibers 1 inside of the tube, free of the resin and shrink tubing.

The packing operation can be conducted on a column or tubing of any desired length. Thus, long tubes can be packed and cut into various lengths for utilization in reactors of different sizes. The resulting tubes have bundles of fibers packed within the tube that may be packed to densities of 70 percent or more of the maximum theoretical packing density for a packed column of a given diameter using fibers of the diameter utilized in preparing the tube.

In a second and preferred alternative, tubes are packed with glass fibers utilizing a cold draw, metal tubing process in which glass fibers to be utilized in a reaction vessel are placed inside of a metal tube that can be reduced in size by passing it through a die to effect reduction of tube diameter and wall thickness.

Figure 7:
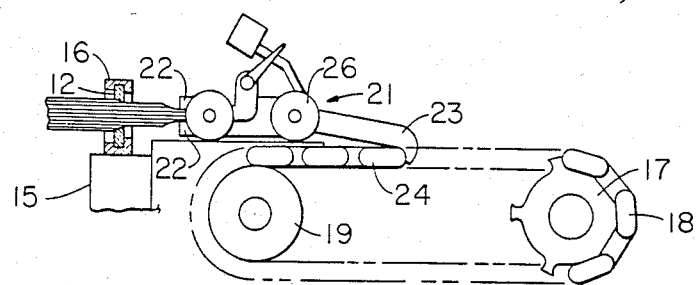
FIG. 7 is a cold drawn tubing reducing system utilized in the second and preferred method utilized for packing the novel reaction tubes of the instant invention.
Figure 8:
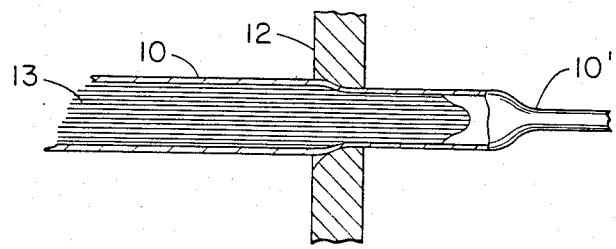
FIG. 8 is an enlarged, side elevation in section of the tube and die shown in FIG. 6.

In preparing packed tubes in accordance with this preferred method, reference is made to the drawings and to FIGS. 7–10. Turning to FIGS. 7 and 8 in particular, a tube 10 such as that shown in FIG. 8 is employed. The tube 10, as shown in FIG. 8, is packed with fibers 13 by inserting fibers into the tube to fill the volume of the tube 10 as much as possible with the fibers 13. The fibers 13 are oriented. generally parallel with respect to each other and to the long axis of the tube 10. Some twisting of the fibers can be employed to effect more fluid interchange between the flow chamber formed by adjacent fibers. In doing this, the ends of the fibers terminate at the constricted neck portion 10' of the tube 10. The tube 10 is pinched in the reduced cross-sectional area 10' so that it can be inserted into the die 12 of FIG. 7 utilized to conduct the tube reduction. After packing the tube 10 with the fibers 13, the pointed end 10' of the tube 10 is passed through the reducing die 12. The die 12 is mounted on a heavy steel frame 15 or bench with the die 12 being held in a die head 16. The draw bench is also provided with a sprocket wheel 17 over which passes a heavy, square link chain 18. The chain 18 lies in a trough on top of the bench 15 which extends from the sprocket wheel 17 to the die head 16 where the chain 18 passes around an idler 19 and returns underneath the bench to the sprocket wheel 17. The sprocket wheel 17 is driven by a variable speed motor through suitable reduction gearing not shown. The carriage 21, called the plier, runs on tracks on top of the bench and over the chain 18 that lies in the trough between the tracks. This plier 21 is equipped at one end with jaws 22 to grip the tube 10 at the restricted end portion 10' thereof and on the other end with a hook 23 to engage the links 24 of the draw chain 18. The plier 21 is connected by a cable not shown to a motor actuated drum 26 by which means it is returned to the die head 16 after drawing the tube 10. The jaws 22 grip the reduced or pointed end of the tube 10 which projects through the die 11 about 6 inches. The closing of the jaws 22 is effected by the motion of the hook 23 in dropping into engagement with the chain 18. The whole action of gripping the tube 10 and engaging the chain 18 is therefore automatic once the operator pushes a button to return the plier 21 to a gripping position.

The benches 15 utilized can be any length but generally are 80 to 100 feet in length and have a capacity of normally of drawing 50,000 to 400,000 lbs. of pulling force on the tubes 10. The chain speed may vary depending on the extent of reduction desired, typically from 20 to 150 feet per minute, and is automatically controlled so that the tube 10 is started through the die 11 at a slow speed and as soon as it is fairly well started, the speed is increased to its predetermined drawing rate.

Using this system, the tube 10 packed with the fibers 13 has its end 10' inserted into the reducing die 11, the jaw 22 grips the end of the tube 10 and pulls the tube 10 through die 11. In passing through the die, the tube 10 is reduced in diameter a sufficient amount to achieve a packing density of between 70 to 100 percent of the theoretical maximum in the finished tube. The method of determining this packing density will be hereinafter described.

Figure 9:
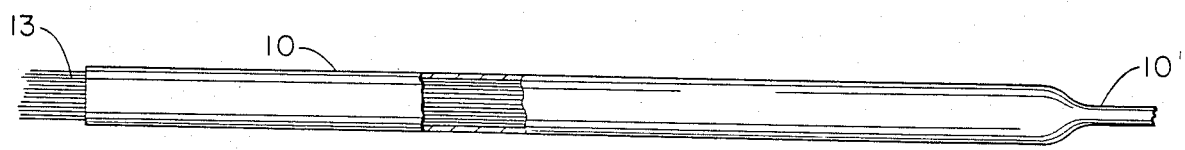
FIG. 9 is a side elevation of a tube reduced by the apparatus of FIG. 6, partly in section, to illustrate fiber orientation.

The reduction of the tube 10 to provide the end 10' shown in FIGS. 7-9 is typically done on rotary swagers or by utilizing steam or air hammers after the end of the tube 10 has been heated to a forging heat.

The tube 10 after the packing operation has been completed is shown in FIG. 9. The last step in the operation involves removing the pointed end 10'. This is done by cutting it off and the tube is then cut into desired lengths, one of such finished tubes being shown in FIG. 10.

Determining Fiber Packing Density

For convenience, fibers may be packed in columns for use in preparing the packed tubes of the instant invention using applicant's methods on a weight basis. This method of determining fibers to be employed for a given column eliminates the necessity of fiber counting and can accurately determine the proper size of a fiber bundle to be used in a tube of desired final size.

To calculate the proper fiber bundle to be placed in a tube of predetermined inside diameter after drawing, the outside diameter of the fiber is measured. The desired final tube internal diameter is then chosen. Since the fibers are generally cylindrical in shape and will rest against each other in bundle form, a fill factor of 0.9069 is used which, when multiplied with the cross sectional area of the tube chosen, will give the available tube cross sectional area available for packing based on triangular-pitch packing, which is the most dense packing possible for fibers of circular cross-section. By dividing the available cross sectional area of the column available for packing by the cross sectional area of the fiber to be employed, the number of fibers necessary to fill that area is readily determined. This number is then used to determine the total volume of fibers that will be needed to fill the cross sectional area of the chosen size tube over a given length by multiplying the cross sectional area of the tube by the length of the column to be filled. The weight of the fibers is then readily determined by multiplying the volume of fibers to be employed by the fiber density of the glass.

These determinations will give the theoretical maximum packing density for a column or tube of given diameter. Variations in the density desired for a given tube can thus be varied from the theoretical 100 percent fill obtained using these calculations to any percentage below that that the user desires. This density will vary depending on the desired use to which the tube is to be put as described in the objectives of the invention.

In the following examples, the novel packed tubes of the instant invention are shown prepared by the preferred method embodiment shown diagrammatically by FIGS. 7-10.

EXAMPLE I

A 10 inch long packed tube having an external diameter of 0.248 inch and an internal diameter of 0.193 inch and containing a packing of parallel glass fibers oriented in parallel with the tube was prepared. The fibers employed to provide the tube packing were substantially the same and had outside diameters (OD) of $7.00 \times 10^{-5}$ cm and had a glass density of 0.7 grams per cubic centimeter.

The cross sectional area of each of the fibers was $3.85 \times 10^{-5}$ cm$^2$. The desired final tube diameter was preselected at 0.490 centimeters. The die 11 was sized to provide this internal diameter from a No. 310 stainless steel tube having an OD of 0.947 cm, an ID of 0.813 cm, and a wall thickness of 0.0685 cm. The stainless steel tube was swaged at the end 10' to permit the swaged portion to pass freely through the die 11. The tube was filled from the constricted swaged end to a length of 25.4 cm with 3.038 grams of the fibers. The fibers were inserted by hand and were aligned parallel to each other and the walls of the tube. The weight of the fibers used was determined by calculating the number of fibers to be used using the equation $N = A/A'$ where $A' = 3.85 \times 10^{-5}$ cm$^2$ and $A = 0.189$ cm$^2 \times 0.907$ (fill factor) or 0.171 cm$^2$. The determined number of fibers using the equation was $4.44 \times 10^3$. Since the desired final packed tube length was 25.4 cm, the fiber weight necessary was calculated using the equation $WT = N \times D \times V$, where $N$ = number of fibers, $D$ = the glass density of each fiber and $V$ = the volume of a fiber 28 cm long. This equation thus was used as follows:

$$WT = 4.44 \times 10^3 \text{ Fib} \times 0.7 \text{ gm/cc} \times 9.78 \times 10^{-4}$$
$$cc = 3.038 \text{ gms Fib}$$

After loading the tube 10 with the requisite fiber weight, the jaws 22 of the carriage 21 were engaged on the end 10' of tube 10' and hook 23 engaged in chain 8. The motor, not shown, was energized and pulling force was applied to draw tube 10 through the die 11. This reduced the OD of tube 10 to 0.629 cm, provided a wall thickness of 0.073 cm and an ID of 0.490 cm.

EXAMPLE II

A second tube was prepared to provide a 2.34 ID packed tube using again fibers each of which had nominal OD of 0.007 cm. The cross sectional area of each of the fibers was thus $3.85 \times 10^{-5}$ cm$^2$. A new die 11 was selected to provide the desired internal diameter from a No. 310 stainless steel tube which had an internal OD of 3.175 cm, an ID of 3 cm and a wall thickness of 1.016 cm. The stainless steel tube 10 was swaged at the end 10' to permit it to be passed freely through the die 11. The tube was then filled with 69.11 gm of glass fibers, the fibers being 25.4 inches in length. Using the equation $$N = A/A' \text{ where } A' = 3.85 \times 10^{-5} \text{ cm}^2$$

and A = 4.289 cm$^2$ × 0.907 (fill factor) or 3.89 cm$^2$. The number of fibers needed was $101 \times 10^5$. The volume of a single fiber 25.4 cm in length was then determined to be $9.78 \times 10^{-4}$ cc. Using the equation WT = (V) × (D) × (N) as in Example I and solving it with the requisite determined values results in the following $$WT = 9.78 \times 10^{-4} cc \times 0.7 \text{ gm/cc} \times 101 \times 10^5 = 69.110 \text{ gm.}$$

Figure 10:
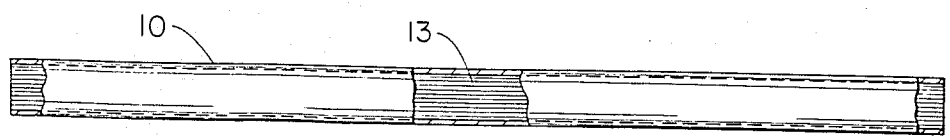
FIG. 10 is a side elevation, partially in section of a finished packed tube of the instant invention illustrating the fiber orientation.

The weighed requisite 69.11 gms of fibers was inserted into the tube and occupied 25.4 cm of the original tube length beyond the constricted area where it was swaged. As in the previous example, the jaws 22 were fastened to the swaged area 10' of tube 10, the hook 23 was dropped into the chain 18 and the motor driven sprocket 17 was energized to pull tube 10 through the die 12 until the tube containing the fibers had passed through the die. The swaged end was cut off and the other end was cut to provide a tube 25.4 cm in length. The final tube as depicted by FIG. 10 had a final ID of 2.34 cm, an OD of 2.537 cm and a wall thickness of 0.102 cm.

Packed tubes can be prepared containing less than the quantity required for a 100 percent of theoretical fill as shown in the example using the same calculations with an appropriate reduction in the number of fibers required for a 100 percent fill being made in determining the final weight to be employed.

One advantage of the preferred method of packing tubes is that the fibers in the tube can be treated before the tube is reduced in diameter. Thus, for example, in a system designed to produce a packed metal tube of glass fibers which are also porous, the tube is packed in the normal manner before reduction in diameter. That tube may then be placed in a hot air oven and heated with the fibers contained in it to phase separate a phase separable glass fiber. The tube can then be removed and can be leached using conventional leaching techniques to provide the desired porosity to the glass fibers. After leaching, the fibers are washed and the tube and its fibers then can be subjected to the cold draw process depicted in FIG. 7 to provide the high density packing desired.

Whole heat treatment of the fibers is not required, i.e., when "E" glass fibers are used, the tubes packed with the fibers are leached with acid as is conventional in the art, washed after leaching and then subjected to the tube redrawing step of FIG. 7 to provide the desired dense packing.

The packed tubes may be used for a variety of purposes and the glass fibers used can be tailored both in composition and physical properties to a particular application. Porous fibers, for example, can be employed where it is desired by rendering the fibers porous using various leaching techniques known in the art. The process can also be applied to fibers other than glass such as cellulosic and organic fibers to achieve packing densities heretofore not possible. Care should be taken regardless of the fibers employed to not exceed the packing density limit of the tubes employed since overfilling has been found to disturb the tube wall surface and in some instances, resulted in rupture of the wall. While the preferred method utilized a steel tube, other tubular metal stock capable of being drawn can be employed. It would also be within the purview of the invention to provide the novel tubes of the invention by, for example, using a thermoplastic tube and a heated die provided the fibers being packed would not be damaged by the heat employed to soften the resin during drawing. While tubes of a cylindrical shape have been used in the illustrative embodiments, other shaped tubes can be used such as triangular, rectangular and oval shapes without departing from the spirit of the invention.

Thus, while the invention has been described with reference to certain specific embodiments, it is not intended to be limited thereby except insofar as it appears in the following claims.

I claim:

1. In a process of packing leached, porous glass fibers in an elongated non-porous wall metal tube, the improvement comprising filling the tube with said leached, porous glass fibers oriented in parallel with respect to each other and with respect to the long axis of the tube, said tube being of a diameter in excess of the final desired diameter of the tube, passing the tube with the leached, porous glass fibers packed therein through a die, reducing the internal diameter of the tube by pulling it through the die in a cold drawing process to reduce the tube to an internal diameter such that the packing density of the leached, porous glass fibers contained in the finished tube after it emerges from the die is between 70 and 100 percent of the theoretical maximum density based on the diameter of the leached, porous glass fibers employed and the final diameter of the tube using a triangular pitch pattern packing method.

2. In a process for packing porous glass fibers in a tube, the improvement comprising filling a non-porous wall metal tube with glass fibers oriented in parallel with respect to each other and with respect to the tube, heating the glass fiber filled tube to a temperature sufficient to phase separate the glass fibers into an extractable phase and a non-extractable phase, leaching the glass fibers contained in the tube by passing mineral acid therethrough to leach the extractable phase from the glass fibers, washing the glass fibers after leaching to remove any residual acid therefrom and thereby provide porous glass fibers in said tube, passing the tube with the resulting leached porous glass fibers through a die and cold drawing the tube into a tube of a final internal diameter such that fibers are packed to a density of 70 to 100 percent of the theoretical maximum packing density for a tube of that final diameter basis the diameter of the glass fibers employed using a triangular pitch pattern packing method.

3. In a process of packing hollow glass fibers in an elongated non-porus wall metal tube, the improvement comprising filling the tube with hollow glass fibers oriented in parallel with respect to each other and with respect to the long axis of the tube, said tube having a diameter in excess of the desired final diameter of the tube, passing the tube having the hollow glass fibers packed therein through a die, reducing the diameter of the tube by pulling it through the die in a cold drawing process to reduce the diameter of the tube to an internal diameter such that the packing density of the hollow glass fibers in the finished tube is between 70 and 100 percent of the theoretical maximum density based on the diameter of the hollow glass fibers the final diameter of the tube and a triangular pitch pattern of packing.

* * * * *